United States Patent [19]

Eggensperger et al.

[11] 3,950,382

[45] Apr. 13, 1976

[54] BIS(4-HYDROXY-3,5-DIALKYLBENZYL)-CYANO-CARBOXYLIC ACID ESTERS

[75] Inventors: Heinz Eggensperger, Gadernheim uber Bensheim; Volker Franzen, Heidelberg; Karl-Heinz Diehl, Benxheim; Wilfred Kloss, Kolmbach uber Bensheim, all of Germany

[73] Assignee: Ciba-Geigy Corporation, Ardsley, N.Y.

[22] Filed: Oct. 1, 1974

[21] Appl. No.: 511,078

Related U.S. Application Data

[60] Division of Ser. No. 211,125, Dec. 22, 1971, Pat. No. 3,856,846, which is a continuation-in-part of Ser. No. 714,100, March 18, 1968, Pat. No. 3,646,110.

[52] U.S. Cl............................................. 260/465 D
[51] Int. Cl.².................................... C07C 121/76
[58] Field of Search................................ 260/465 D

[56] References Cited
UNITED STATES PATENTS

| | | | |
|---|---|---|---|
| 3,054,822 | 9/1962 | Schorr et al. | 260/465 X |
| 3,721,704 | 3/1973 | Dexter | 260/465 XR |

*Primary Examiner*—Lewis Gotts
*Assistant Examiner*—Dolph H. Torrence
*Attorney, Agent, or Firm*—Fisher, Christen & Sabol

[57] ABSTRACT

The reaction of one mole of a Mannich base corresponding to the formula

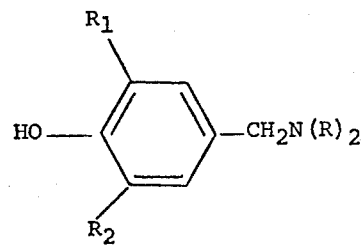

and one mole of a Mannich base corresponding to the formula

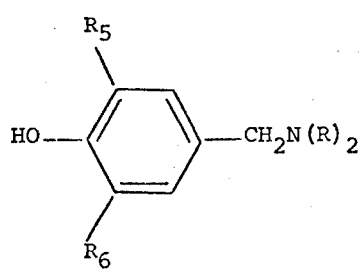

wherein $R_1$, $R_2$, $R_4$ and $R_5$ are independently selected from alkyl groups having 1 to 6 carbon atoms and R is alkyl, preferably lower alkyl, with 1 mole of a carboxylic acid ester corresponding to the formula $R_3CH_2COOR_4$ wherein $R_3$ is —H, —CN or —COOR$_4$ and $R_4$ is an alkyl, thioether, oxyether or aralkyl group having up to 20 carbons in the presence of a catalytically effective amount of an alkaline catalyst is useful for preparing compounds corresponding to the formula

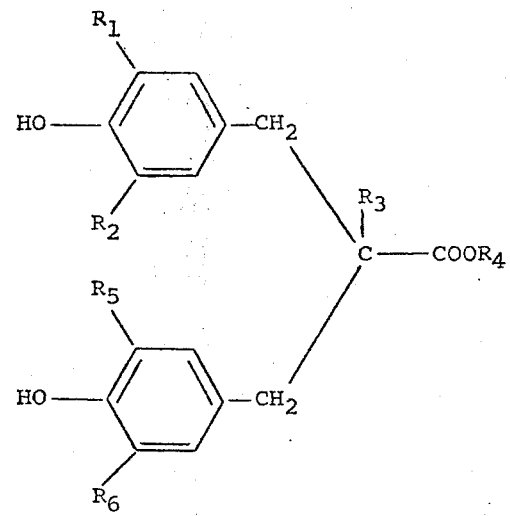

The compounds represented by the above formula are useful as stabilizers for synthetic resins, particularly polyolefins. Compounds of the above formula, when $R_3$ is —CN are novel and may also be prepared by reacting 1 mole of

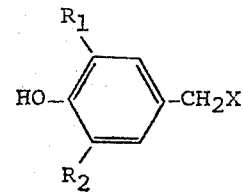

and 1 mole of

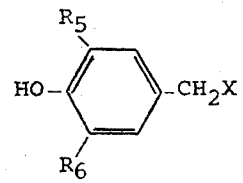

wherein X is halogen with 1 mole of NCCH$_2$COOR$_4$ in the presence of an alkali metal and an anhydrous inert organic solvent.

7 Claims, No Drawings

BIS(4-HYDROXY-3,5-DIALKYLBENZYL)CYANO-CARBOXYLIC ACID ESTERS

This application is a division of application Ser. No. 211,125 filed Dec. 22, 1971 now U.S. Pat. No. 3,856,846, which application in turn was a continuation-in-part of application Ser. No. 714,100, filed Mar. 18, 1968 now U.S. Pat. No. 3,646,110.

This invention relates to a novel process of preparing dialkyl benzyl carboxylic esters, certain novel compounds and resins stabilized therewith.

Esters of the formula

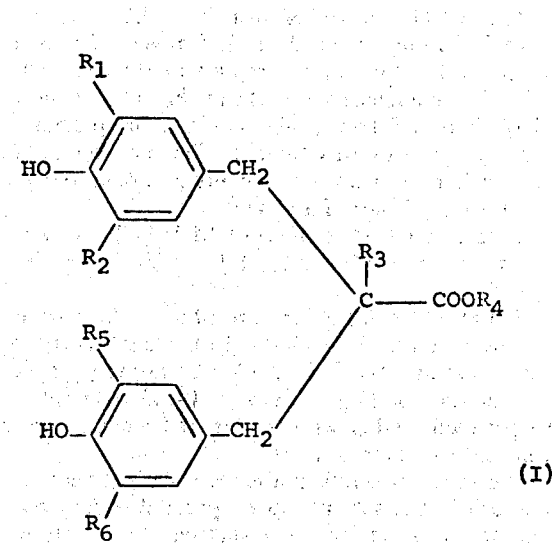

wherein $R_1$, $R_2$, $R_5$ and $R_6$ are the same or different linear or branched alkyl groups having 1 to 6 carbon atoms, $R_3$ is —H, —CN, or —COOR$_4$, and $R_4$ is a linear, branched, cyclic, saturated or unsaturated alkyl, thioether, ether, or aralkyl group, having 1 to 20 carbon atoms can be prepared by reacting in an inert organic solvent one mole of a Mannich base of the formula

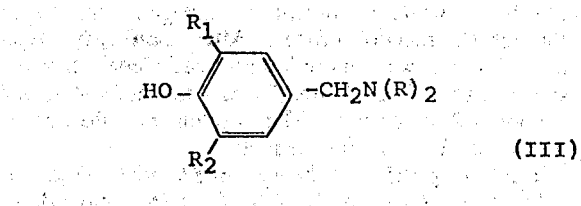

and one mole of a Mannich base of the formula

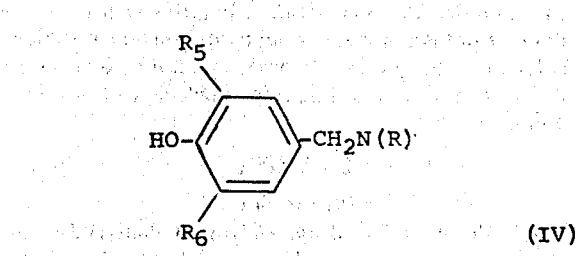

wherein $R_1$, $R_2$, $R_5$ and $R_6$ are as defined above with one mole of a carboxylic acid ester of the formula $R_3$—CH$_2$—COOR$_4$, wherein $R_3$ and $R_4$ are as defined above and R is preferably lower alkyl in the presence of a catalytic amount of an alkaline compound selected from alkali metal compounds and alkaline earth metal compounds. When $R_1$ is the same as $R_5$ and $R_2$ is the same as $R_6$, the reaction may be conducted in a single step by reacting two moles of the Mannich base with one mole of the carboxylic acid ester. Suitable alkaline compounds include the oxides, hydroxides, amides, hydrides and alcoholates of alkali and alkaline earth metals such as, lithium, sodium, potassium, calcium, magnesium and barium. Specific examples of suitable compounds include lithium, sodium and barium oxides; sodium, potassium, calcium, magnesium and barium hydroxides; sodium, lithium, calcium, magnesium, and barium hydrides; sodium amide, sodium acetamide, lithium amide and magnesium amide; and sodium methylate, sodium ethylate, sodium propylate, sodium phenate, potassium phenate, calcium ethylate, magnesium methylate, magnesium ethylate and barium ethylate as well as mixtures thereof.

The Mannich bases react almost quantitatively with the carboxylic acid esters and the Mannich bases are readily prepared by the well known reaction of phenols, formaldehyde, and secondary amines, such as dimethylamine. Therefore, this process of the present invention provides a very economic procedure.

A preferred method for the preparation of symmetrical bis-products from Mannich bases consists in refluxing two moles of a Mannich base when $R_1$ is the same as $R_5$ and $R_2$ is the same as $R_6$ with 1 mole of carboxylic acid ester (malonic acid ester, cyanoacetic acid ester) at 60° to 250°C. in the presence of 1 to 20 g of an alkali metal or alkaline earth metal alcoholate in a suitable solvent, e.g., in 1 liter of toluene, under nitrogen for ½ to 4 hours. When the reaction is terminated, the reaction mixture is cooled and the reaction product is recovered. For this purpose, the catalyst is first removed, e.g., by neutralization with dilute acid and shaking out with water, and then the reaction solution is dried. The solvent is distilled off under reduced pressure and the residue may be purified by recrystallization. The yield is generally about 80 to 99 percent.

In the preparation of the asymmetrical bis-products, which are particularly effective stabilizers, one mole of carboxylic acid ester is reacted with one mole of a Mannich base according to the following equation to form an intermediate compound

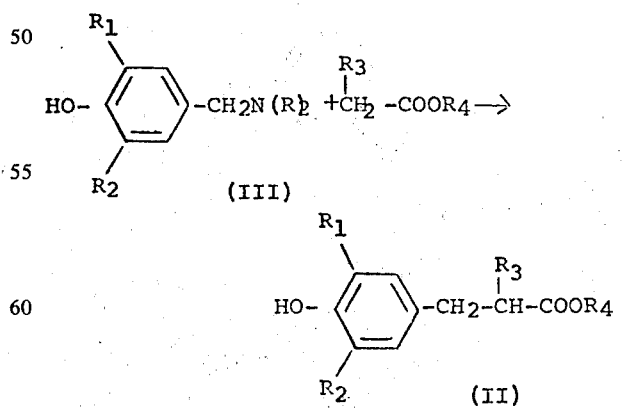

This compound is then further reacted with one mole of a Mannich base having different alkyl group than the first Mannich base to form the product. Both reactions can be carried out in the same reaction vessel similar to the procedure described above for the preparation of the symmetrical compounds. In the case of the asymmetrical compounds, the two Mannich bases are added to the reaction vessel successively for refluxing whereby the second Mannich base is generally added about 2 hours after the first base.

The reaction here involved is a "C-alkylation" of the phenol Mannich bases to disubstituted malonic acid or cyanoacetic acid esters. The literature indicated that such C-alkylation would be possible only when the difficulty available ammonium salts of the phenol-Mannich base are used as starting material (see H. Hellmann and G. Opitz, "α-Aminoalkylation", 1960, p. 284). It was not to be expected that the reaction described herein would be possible and would smoothly produce the novel malonic and cyanoacetic esters of the phenol Mannich bases.

The bis-(4-hydroxy-3,5-dialkyl-benzyl) mono-carboxylic ester compounds of formula I, wherein $R_3 = H$, are obtained by saponification and decarboxylation of the corresponding cyanoacetic or malonic acid esters.

Compounds of the formula

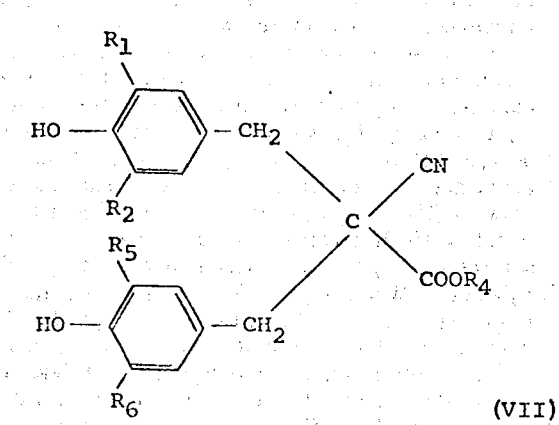

wherein $R_1$, $R_2$, $R_4$, $R_5$ and $R_6$ are as defined above are novel. These compounds may be prepared by the novel process described above or can be prepared by reacting, in the presence of an anhydrous inert organic solvent and an alkali metal, 1 mole of

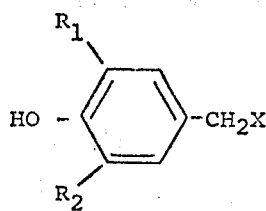

and 1 mole of

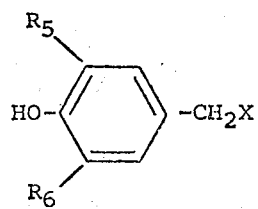

wherein X is halogen with 1 mole of cyanocarboxylic acid ester of the formula $NCCH_2COOR_4$.

Anhydrous inert solvents which are suitable include aromatic hydrocarbons, aliphatic hydrocarbons, glycol ethers, other high boiling ethers and alcohols of the formula $R_4OH$, wherein $R_4$ is as defined hereinabove. Aromatic hydrocarbons are the preferred solvents.

Suitable alkali metals include lithium, sodium and potassium and sodium is especially preferred.

The following examples are given to illustrate the invention but not to limit the scope of the invention.

EXAMPLE 1

Preparation of Bis-(4-Hydroxy-3,5-Di-Tert. Butyl 4-Hydroxybenzyl) Cyanoacetic Acid Ethyl Ester.

A. 263.4 G (1 mole) of (4-hydroxy-3,5-di-tert.butylbenzyl) dimethylamine, 51 g (0.45 moles) of cyanoacetic acid ethylester, 3 g of magnesium ethylate, and 5 g of sodium methylate were refluxed in 1 liter of absolute alcohol for 1.5 hours; after cooling, the precipitated reaction product was filtered. The reaction product was shaken out with 96% alcohol and once recrystallized from 1.5 liter of acetone.

Yield: 255 g (99% of theory): M 212°–213°C. Analysis: found: C, 76.3%; H, 9.13%; calc. C, 76.3%; H, 9.35%.

B. 300 G (1mole) of 3,5-di-tert-butyl-4-hydroxy-benzyl bromide and 56 g (0.5 moles) of cyanoacetic acid ethyl ester in 500 CC of petroleum ether were added to a suspension of 23 g (1 g atom) of sodium in 1600 CC of petroleum ether with stirring and the mixture was refluxed for about 3 hours.

The reaction solution was then washed with water and dried. The solvent was evaporated under vacuum and the product was recrystallized from petroleum ether.

EXAMPLE 2

Preparation of Bis-(4-Hydroxy-3-Methyl-5-Tert. Butylbenzyl) Malonic Acid Distearyl Ester (Stabilizer I)

27.6 G (0.125 mole) of (4-hydroxy-3-methyl-5-tert. butylbenzyl) dimethylamine, 30.5 g (0.05 mole) of malonic acid distearyl ester, and 0.5 g of sodium methylate were refluxed in 100 cc of absolute toluene for 2½ hours while a current of nitrogen was passed through the reaction mixture. After cooling, the reaction mixture was diluted with methylene chloride, shaken out with 2N hydrochloric acid and water, and evaporated to dryness. The residue was slurried in methanol, filtered, and washed.

Yield: 41 g (85% of theory): m 83°–90°C. Analysis: calc.: C, 78.69%; H, 11.32%; 0, 9.98%. Found: C, 79.25%; H, 10.66%; 0, 9.99%.

This reaction also proceeds as described above with substantially the same yields if hydroxides such as sodium or potassium hydroxide; hydrides such as lithium, calcium or magnesium hydride or amides such as sodium or magnesium amide are used instead of the alcoholate.

EXAMPLE 3

Preparation of 1-(3-Methyl-5-Tert.Butyl-4-Hydroxyphenyl)-3-(3,5-Di-Isopropyl-4-Hydroxyphenyl)-2,2-Bis-Carbostearoxy Propane 4.4G (0.02 mole) of (4-hydroxy-3-methyl-5-tert.butylbenzyl)-dimethylamine, 12.2 g (0.02 mole) of malonic acid distearyl ester, and 0.2 g of sodium methylate in 100 cc of absolute xylene were refluxed under nitrogen for 2 hours. Subsequently, 5 g (0.213 moles) of (4-hydroxy-3,5-diisopropylbenzyl)-dimethylamine were added, and the mixture was again refluxed for 1½ hours. After cooling, the reaction mixture was shaken out first with 2N hydrochloric acid, then with water, dried, and the solvent was evaporated in vacuo. After recrystallization from an isopropanol-methanol mixture, there were obtained 16 g (82% of theory) of the reaction product, m 90°–93°C.

Analysis: Calc.: C, 78.79%; H, 11.37%; 0, 9.84%. Found: C, 78.72%; H, 11.09%; 0, 9.90%.

EXAMPLE 4

Preparation of
Bis-(3,5-Di-Tert.Butyl-4-Hydroxybenzyl)-Malonic Acid-Di-(3-HexylMercapto)-Propylester (Stabilizer II)

By reaction of the Mannich base of 2,6-di-tert.butylphenol with malonic acid di(3-hexyl-mercapto) propyl ester, 23 g (0.055 mole) of malonic acid di(3-hexyl-mercapto) propyl ester, 32.8 g (0.125 mole) of the Mannich base of 2,5-ditertiary butylphenol, and 0.5 g of sodium methylate were refluxed in 100 cc of absolute toluene for 1.5 hours, and, after cooling, washed with 2N hydrochloric acid, dried and concentrated to dryness. The residue was twice recrystallized from petrol ether.

Yield: 36.9 g = 80% of theory. Analysis: calc.: C, 73.08%; H, 7.82%; 0, 11.45%; S, 7.65%. Found: C, 72.76%; H, 8.03%; 0, 11.22%; S, 7.47%. M.P. 84°–86°C.

Some of the compounds prepared in an analogous manner, are: bis-(3,5-di-tert.butyl-4-hydroxybenzyl) malonic acid di(3-laurylmercapto) propyl ester (Stabilizer III); m 71°–73°C; yield 70%; α-(4-hydroxy-3,5-di-tert.butylbenzyl)-α'-(4-hydroxy-3-tert.butyl-5-methylbenzyl)-malonic acid distearyl ester (Stabilizer IV) m 87°–90°C; yield 81%.

Examples of other compounds which are prepared in the same way are listed in Table I, where they are defined by their substituents according to formula I. Their structure, can be determined, by their molecular-weight, IR spectra, and quantitative analysis. The melting points of some specific compounds are also given in degrees C. under the column M.P. Those compounds in which the $R_4$ group is followed by a number in parenthesis are used in tests of other examples and are identified by this number.

TABLE I

| $R_1$ | $R_2$ | $R_5$ | $R_6$ | $R_3$ | $R_4$ | M.P. |
|---|---|---|---|---|---|---|
| —$CH_3$ | —$CH_3$ | —$CH_3$ | —$CH_3$ | —CN | —$CH_3$ | |
| " | " | " | " | —$COOR_4$ | " | |
| " | " | " | " | —CN | —$C_2H_5$ | 197–199 |
| " | " | " | " | —$COOR_4$ | " | 190–192 |
| " | " | " | " | —CN | —$CH_2(CH_3)_2$ | |
| " | " | " | " | —$COOR_4$ | " | |
| " | " | " | " | —CN | —$C_4H_9$ | |
| " | " | " | " | —$COOR_4$ | " | |
| " | " | " | " | —CN | —$C(CH_3)_3$ | |
| " | " | " | " | —$COOR_4$ | " | |
| " | " | " | " | —CN | —$CH_2CH(CH_3)_2$ | |
| " | " | " | " | —$COOR_4$ | " | |
| " | " | " | " | —CN | —$C_6H_{13}$ | |
| " | " | " | " | —$COOR_4$ | " | |
| " | " | " | " | —CN | —$C_8H_{17}$ | |
| " | " | " | " | —$COOR_4$ | " | |
| " | " | " | " | —CN | —$CH_2CH(C_2H_5)(CH_2)_3CH_3$ | |
| " | " | " | " | —$COOR_4$ | " | |
| " | " | " | " | —CN | —$C_{12}H_{25}$ | |
| " | " | " | " | —$COOR_4$ | " | 78 |
| " | " | " | " | —CN | —$C_{20}H_{41}$ | |
| " | " | " | " | —$COOR_4$ | " | |
| " | " | " | " | —CN | —$C_{16}H_{33}$ | |
| " | " | " | " | —$COOR_4$ | " | |
| " | " | " | " | —CN | —$C_{18}H_{37}$ | |
| " | " | " | " | —$COOR_4$ | " | 90 |
| " | " | " | " | —CN | —⟨H⟩ (phenyl) | |
| " | " | " | " | —$COOR_4$ | " | |
| " | " | " | " | —CN | —$CH_2$—⟨phenyl⟩ | |
| " | " | " | " | —$COOR_4$ | " | |
| " | " | " | " | —CN | —$CH_2CH_2$—⟨phenyl⟩ | |
| " | " | " | " | —$COOR_4$ | " | |
| $CH_3$ | $CH_3$ | t.butyl | t.butyl | —CN | —$CH_3$ | 146 |
| " | " | " | " | —$COOR_4$ | " | |
| " | " | " | " | —CN | —$C_2H_5$ | |
| " | " | " | " | —$COOR_4$ | " | |
| " | " | " | " | —CN | —$CH_2(CH_3)_2$ | |
| t.butyl | t.butyl | i.propyl | i.propyl | —$COOR_4$ | " | |
| " | " | " | " | —CN | —$C_4H_9$ | |
| " | " | " | " | —$COOR_4$ | " | |
| i.propyl | i.propyl | " | " | —CN | —$C(CH_3)_3$ | |
| " | " | " | " | —$COOR_4$ | " | |
| " | " | " | " | —CN | —$CH_2CH(CH_3)_2$ | |

TABLE I-continued

| R₁ | R₂ | R₅ | R₆ | R₃ | R₄ | M.P. |
|---|---|---|---|---|---|---|
| " | " | " | " | —COOR₄ | " | |
| " | " | " | " | —CN | —C₆H₁₃ | |
| " | " | " | " | —COOR₄ | " | |
| " | " | " | " | —CN | —C₈H₁₇ | |
| " | " | " | " | —COOR₄ | " | |
| " | " | " | " | —CN | CH₂CH(C₂H₅)(CH₂)₃CH₃ | |
| " | " | " | " | —COOR₄ | " | |
| " | " | " | " | —CN | —C₁₂H₂₅ | 166–168 |
| CH₃ | CH₃ | t.butyl | t.butyl | —COOR₄ | " | 82 |
| " | " | " | " | —CN | —C₁₆H₃₃ | |
| " | " | " | " | —COOR₄ | " | |
| i.propyl | i.propyl | i.propyl | i.propyl | —CN | —C₁₈H₃₇ | |
| " | " | " | " | —COOR₄ | " | 103–104 |
| " | " | " | " | —CN |  | |
| " | " | " | " | —COOR₄ | " | |
| " | " | " | " | —CN |  | |
| " | " | " | " | —COOR₄ | " | |
| " | " | " | " | —CN |  | |
| " | " | " | " | —COOR₄ | " | |
| —CH₃ | t.butyl | t.butyl | t.butyl | —CN | —CH₃ | |
| " | " | " | " | —COOR₄ | " | |
| " | " | " | " | —CN | —C₂H₅ | |
| " | " | " | " | —COOR₄ | " | |
| " | " | " | " | —CN | —CH₂(CH₃)₂ | |
| " | " | " | " | —COOR₄ | " | |
| " | " | " | " | —CN | —C₄H₉ | |
| " | " | " | " | —COOR₄ | " | |
| " | " | " | " | —CN | —C(CH₃)₃ | |
| " | " | " | " | —COOR₄ | " | |
| " | " | " | " | —CN | —CH₂CH(CH₃)₂ | |
| " | " | " | " | —COOR₄ | " | |
| " | " | " | " | —CN | —C₆H₁₃ | |
| " | " | " | " | —COOR₄ | " | |
| " | " | " | " | —CN | —C₈H₁₇ | |
| " | " | " | " | —COOR₄ | " | |
| " | " | " | " | —CN | —CH₂CH(C₂H₅)(CH₂)₃CH₃ | |
| " | " | " | " | —COOR₄ | " | |
| " | " | " | " | —CN | —C₁₂H₂₅ | |
| " | " | " | " | —COOR₄ | " | |
| " | " | " | " | —CN | —C₁₆H₃₃ | |
| " | " | " | " | —COOR₄ | " | |
| " | " | " | " | —CN | —C₁₈H₃₇ | |
| " | " | " | " | —COOR₄ | " | |
| " | " | " | " | —CN | —C₂₀H₄₁ | |
| " | " | " | " | —COOR₄ | " | |
| " | " | " | " | —CN |  | |
| " | " | " | " | —COOR₄ | " | |
| " | " | " | " | —CN | —CH₂<phenyl> | |
| " | " | " | " | —COOR₄ | " | |
| " | " | " | " | —CN |  | |
| " | " | " | " | —COOR₄ | " | |
| " | —CH₃ | —CH₃ | " | —CN | —CH₃ | |
| " | " | " | " | —COOR₄ | " | |
| " | " | " | " | —CN | —C₂H₅ | |
| " | " | " | " | —COOR₄ | " | |
| " | " | " | " | —CN | —CH₂(CH₃)₂ | |
| " | " | " | " | —COOR₄ | " | |
| " | " | " | " | —CN | —C₄H₉ | |
| " | " | " | " | —COOR₄ | " | |
| " | " | " | " | —CN | —C(CH₃)₃ | |
| " | " | " | " | —COOR₄ | " | |
| " | " | " | " | —CN | —CH₂CH(CH₃)₂ | |
| " | " | " | " | —COOR₄ | " | |

TABLE I-continued

| R₁ | R₂ | R₅ | R₆ | R₃ | R₄ | M.P. |
|---|---|---|---|---|---|---|
| ″ | ″ | ″ | ″ | —CN | —C₆H₁₃ | |
| ″ | ″ | ″ | ″ | —COOR₄ | ″ | |
| ″ | ″ | ″ | ″ | —CN | —C₈H₁₇ | |
| ″ | ″ | ″ | ″ | —COOR₄ | ″ | |
| ″ | ″ | ″ | ″ | —CN | —CH₂CH(C₂H₅)(CH₂)₃CH₃ | |
| ″ | ″ | ″ | ″ | —COOR₄ | ″ | |
| ″ | ″ | ″ | ″ | —CN | —C₁₂H₂₅ | |
| ″ | ″ | ″ | ″ | —COOR₄ | ″ | |
| ″ | ″ | ″ | ″ | —CN | —C₂₀H₄₁ | |
| ″ | ″ | ″ | ″ | —COOR₄ | ″ | |
| ″ | ″ | ″ | ″ | —CN | —C₁₆H₃₃ | |
| ″ | ″ | ″ | ″ | —COOR₄ | ″ | |
| ″ | ″ | ″ | ″ | —CN | —C₁₈H₃₇ | |
| ″ | ″ | ″ | ″ | —COOR₄ | ″ | 100 |
| ″ | ″ | ″ | ″ | —CN | —C₆H₁₁ (cyclohexyl) | |
| ″ | ″ | ″ | ″ | —COOR₄ | ″ | |
| ″ | ″ | ″ | ″ | —CN | —CH₂C₆H₅ | |
| ″ | ″ | ″ | ″ | —COOR₄ | ″ | |
| ″ | ″ | ″ | ″ | —CN | —CH₂CH₂C₆H₅ | |
| ″ | ″ | ″ | ″ | —COOR₄ | ″ | |
| CH₃ | t.butyl | CH₃ | ″ | —CN | —CH₃ | |
| ″ | ″ | ″ | ″ | —COOR₄ | ″ | |
| ″ | ″ | ″ | ″ | —CN | —C₂H₅ (6) | 181–182 |
| ″ | ″ | ″ | ″ | —COOR₄ | ″ | 174–175 |
| ″ | ″ | ″ | ″ | —CN | —CH₂(CH₃)₂ | |
| ″ | ″ | ″ | ″ | —COOR₄ | ″ | |
| ″ | ″ | ″ | ″ | —CN | —C₄H₉ | |
| ″ | ″ | ″ | ″ | —COOR₄ | ″ | 128–130 |
| ″ | ″ | ″ | ″ | —CN | —C(CH₃)₃ | |
| ″ | ″ | ″ | ″ | —COOR₄ | ″ | |
| ″ | ″ | ″ | ″ | —CN | —CH₂CH(CH₃)₂ | |
| ″ | ″ | ″ | ″ | —COOR₄ | ″ | |
| ″ | ″ | ″ | ″ | —CN | —C₂₀H₄₁ | |
| ″ | ″ | ″ | ″ | —COOR₄ | ″ | |
| ″ | ″ | ″ | ″ | —CN | —C₆H₁₃ | |
| ″ | ″ | ″ | ″ | —COOR₄ | ″ | 95–97 |
| ″ | ″ | ″ | ″ | —CN | —C₈H₁₇ | |
| ″ | ″ | ″ | ″ | —COOR₄ | ″ (11) | 98–99 |
| ″ | ″ | ″ | ″ | —CN | —CH₂CH(C₂H₅)(CH₂)₃CH₃ | |
| ″ | ″ | ″ | ″ | —COOR₄ | ″ | |
| ″ | ″ | ″ | ″ | —CN | —C₁₂H₂₅ (8) | 104–105 |
| ″ | ″ | ″ | ″ | —COOR₄ | ″ | 88–89 |
| ″ | ″ | ″ | ″ | —CN | —C₁₆H₃₃ | |
| ″ | ″ | ″ | ″ | —COOR₄ | ″ | |
| ″ | ″ | ″ | ″ | —CN | —C₁₈H₃₇ | 72–75 |
| ″ | ″ | ″ | ″ | —COOR₄ | ″ (I) | 83–90 |
| ″ | ″ | ″ | ″ | —CN | —C₆H₁₁ (cyclohexyl) | |
| ″ | ″ | ″ | ″ | —COOR₄ | ″ | |
| ″ | ″ | ″ | ″ | —CN | —CH₂C₆H₅ | |
| ″ | ″ | ″ | ″ | —COOR₄ | ″ | |
| ″ | ″ | ″ | ″ | —CN | —CH₂CH₂C₆H₅ | |
| ″ | ″ | ″ | ″ | —COOR₄ | ″ | |
| t.butyl | ″ | t.butyl | ″ | —CN | —CH₃ | |
| ″ | ″ | ″ | ″ | —COOR₄ | ″ | 170–171 |
| ″ | ″ | ″ | ″ | —CN | —C₂H₅ (7) | 211–212 |
| ″ | ″ | ″ | ″ | —COOR₄ | ″ | |
| ″ | ″ | ″ | ″ | —CN | —CH₂(CH₃)₂ | |
| ″ | ″ | ″ | ″ | —COOR₄ | ″ | |
| ″ | ″ | ″ | ″ | —CN | —C₄H₉ | |
| ″ | ″ | ″ | ″ | —COOR₄ | ″ | |
| ″ | ″ | ″ | ″ | —CN | —C(CH₃)₃ | |
| ″ | ″ | ″ | ″ | —COOR₄ | ″ | |
| ″ | ″ | ″ | ″ | —CN | —CH₂CH(CH₃)₂ | |
| ″ | ″ | ″ | ″ | —COOR₄ | ″ | |
| ″ | ″ | ″ | ″ | —CN | —CH₂—CH=CH₂ | |
| ″ | ″ | ″ | ″ | —COOR₄ | ″ | 135–137 |
| ″ | ″ | ″ | ″ | —CN | —C₆H₁₃ | |

TABLE I-continued

| $R_1$ | $R_2$ | $R_5$ | $R_6$ | $R_3$ | $R_4$ | M.P. |
|---|---|---|---|---|---|---|
| " | " | " | " | —COOR$_4$ | " | |
| " | " | " | " | —CN | —C$_8$H$_{17}$ (12) | |
| " | " | " | " | —COOR$_4$ | " | 104–105 |
| " | " | " | " | —CN | —CH$_2$CH(C$_2$H$_5$)(CH$_2$)$_3$CH$_3$ (13) | |
| " | " | " | " | —COOR$_4$ | " | 114 |
| " | " | " | " | —CN | —C$_{12}$H$_{25}$ (9) | 119–120 |
| " | " | " | " | —COOR$_4$ | " (14) | 112–113 |
| " | " | " | " | —CN | —C$_{16}$H$_{33}$ | |
| " | " | " | " | —COOR$_4$ | " | |
| " | " | " | " | —CN | —C$_{18}$H$_{37}$ | 95–96 |
| " | " | " | " | —COOR$_4$ | " | 98–100 |
| " | " | " | " | —CN | —C$_{20}$H$_{41}$ | |
| " | " | " | " | —COOR$_4$ | " | 93 |
| " | " | " | " | —CN |  | |
| " | " | " | " | —COOR$_4$ | " | 160 |
| " | " | " | " | —CN |  | |
| " | " | " | " | —COOR$_4$ | " | 131–132 |
| " | " | " | " | —CN |  | |
| " | " | " | " | —COOR$_4$ | " | |
| —CH$_3$ | —CH$_3$ | —CH$_3$ | —CH$_3$ | —CN | —C$_2$H$_4$SC$_2$H$_5$ | |
| " | " | " | " | —COOR$_4$ | " | |
| " | " | " | " | —CN | —C$_2$H$_4$SC$_3$H$_7$ | |
| " | " | " | " | —COOR$_4$ | " | |
| " | " | " | " | —CN | —C$_2$H$_4$SCH(CH$_3$)$_2$ | |
| " | " | " | " | —COOR$_4$ | " | |
| " | " | " | " | —CN | —C$_2$H$_4$SC$_4$H$_9$ | |
| " | " | " | " | —COOR$_4$ | " | |
| " | " | " | " | —CN | —C$_2$H$_4$SC$_6$H$_{13}$ | |
| " | " | " | " | —COOR$_4$ | " | |
| " | " | " | " | —CN | —C$_2$H$_4$SC$_8$H$_{17}$ | |
| " | " | " | " | —COOR$_4$ | " | |
| " | " | " | " | —CN | —C$_2$H$_4$SC$_{18}$H$_{37}$ | |
| " | " | " | " | —COOR$_4$ | " | |
| " | " | " | " | —CN | —C$_2$H$_4$SCH$_2$CH(C$_2$H$_5$)—(CH$_2$)$_3$CH$_3$ | |
| " | " | " | " | —COOR$_4$ | " | |
| " | " | " | " | —CN | —C$_2$H$_4$SC$_{12}$H$_{25}$ | |
| " | " | " | " | —COOR$_4$ | " (20) | 68 |
| " | " | " | " | —CN | —C$_2$H$_4$SC$_{16}$H$_{33}$ | |
| " | " | " | " | —COOR$_4$ | " | |
| " | " | " | " | —CN | —C$_3$H$_6$SC$_3$H$_7$ | |
| " | " | " | " | —COOR$_4$ | " | |
| " | " | " | " | —CN | —C$_3$H$_6$SC$_8$H$_{17}$ | |
| " | " | " | " | —COOR$_4$ | " | |
| " | " | " | " | —CN | —C$_3$H$_6$SC$_{12}$H$_{25}$ | |
| " | " | " | " | —COOR$_4$ | " | |
| " | " | " | " | —CN | —C$_3$H$_6$SC$_{16}$H$_{33}$ | |
| " | " | " | " | —COOR$_4$ | " | |
| " | " | " | " | —CN | —C$_4$H$_8$SC$_4$H$_9$ | |
| " | " | " | " | —COOR$_4$ | " | |
| " | " | " | " | —CN | —C$_2$H$_4$SC$_2$H$_4$SC$_2$H$_5$ | |
| " | " | " | " | —COOR$_4$ | " | |
| " | " | " | " | —CN | —C$_4$H$_8$SC$_4$H$_8$SC$_4$H$_9$ | |
| " | " | " | " | —COOR$_4$ | " | |
| " | " | " | " | —CN | —C$_8$H$_{16}$SC$_8$H$_{17}$ | |
| " | " | " | " | —COOR$_4$ | " | |
| T.butyl | T.butyl | T.butyl | T.butyl | —CN | —C$_2$H$_4$SC$_2$H$_5$ | |
| " | " | " | " | —COOR$_4$ | " | |
| " | " | " | " | —CN | —C$_2$H$_4$SC$_3$H$_7$ | |
| " | " | " | " | —COOR$_4$ | " | |
| " | " | " | " | —CN | —C$_2$H$_4$SCH(CH$_3$)$_2$ | |
| " | " | " | " | —COOR$_4$ | " | |
| " | " | " | " | —CN | —C$_2$H$_4$SC$_4$H$_9$ | |
| " | " | " | " | —COOR$_4$ | " | 118–119 |
| " | " | " | " | —CN | —C$_2$H$_4$SC$_6$H$_{13}$ | |
| " | " | " | " | —COOR$_4$ | " | 88–89 |
| " | " | " | " | —CN | —C$_2$H$_4$SC$_8$H$_{17}$ | |
| " | " | " | " | —COOR$_4$ | " | 98–100 |
| " | " | " | " | —CN | —C$_2$H$_4$SCH$_2$CH(C$_2$H$_5$)—(CH$_2$)$_3$CH$_3$ | |
| " | " | " | " | —COOR$_4$ | " | |
| " | " | " | " | —CN | —C$_2$H$_4$SC$_{12}$H$_{25}$ | |
| " | " | " | " | —COOR$_4$ | " (21) | 80 |
| " | " | " | " | —CN | —C$_2$H$_4$SC$_{16}$H$_{33}$ | |
| " | " | " | " | —COOR$_4$ | " (22) | 72–75 |
| " | " | " | " | —CN | —C$_2$H$_4$SC$_{18}$H$_{37}$ | |
| " | " | " | " | —COOR$_4$ | " | |
| " | " | " | " | —CN | —C$_3$H$_6$SC$_6$H$_{13}$ | |
| " | " | " | " | —COOR$_4$ | " (II) | 84–86 |

TABLE I-continued

| R₁ | R₂ | R₅ | R₆ | R₃ | R₄ | M.P. |
|---|---|---|---|---|---|---|
| " | " | " | " | —CN | —C₃H₆SC₈H₁₇ | |
| " | " | " | " | —COOR₄ | " (23) | 82–84 |
| " | " | " | " | —CN | —C₃H₆SC₁₂H₂₅ | |
| " | " | " | " | —COOR₄ | " (III) | 78–79 |
| " | " | " | " | —CN | —C₃H₆SC₁₆H₃₃ | |
| " | " | " | " | —COOR₄ | " (24) | 72–75 |
| " | " | " | " | —CN | —C₄H₈SC₄H₉ | |
| " | " | " | " | —COOR₄ | " | |
| " | " | " | " | —CN | —C₂H₄SC₂H₄SC₂H₅ | |
| " | " | " | " | —COOR₄ | " | |
| " | " | " | " | —CN | —C₄H₈SC₄H₈SC₄H₉ | |
| " | " | " | " | —COOR₄ | " | |
| " | " | " | " | —CN | —C₈H₁₆SC₈H₁₇ | |
| " | " | " | " | —COOR₄ | " | |
| —CH₃ | t.butyl | —CH₃ | t.butyl | —CN | 13 C₂H₄SC₂H₅ | |
| " | " | " | " | —COOR₄ | " | |
| " | " | " | " | —CN | —C₂H₄SC₃H₇ | |
| " | " | " | " | —COOR₄ | " | |
| " | " | " | " | —CN | —C₂H₄SC₁₈H₃₇ | |
| " | " | " | " | —COOR₄ | " | |
| " | " | " | " | —CN | —C₂H₄SCH(CH₃)₂ | |
| " | " | " | " | —COOR₄ | " | |
| " | " | " | " | —CN | —C₂H₄SC₄H₉ | |
| " | " | " | " | —COOR₄ | " | |
| " | " | " | " | —CN | —C₂H₄SC₆H₁₃ | |
| " | " | " | " | —COOR₄ | " | |
| " | " | " | " | —CN | —C₂H₄SC₈H₁₇ | |
| " | " | " | " | —COOR₄ | " | 76–77 |
| " | " | " | " | —CN | —C₂H₄SCH₂CH(C₂H₅)—(CH₂)₃CH₃ | |
| " | " | " | " | —COOR₄ | " | |
| " | " | " | " | —CN | —C₂H₄SC₁₂H₂₅ (10) | 57–58 |
| " | " | " | " | —COOR₄ | " | < 50 |
| " | " | " | " | —CN | —C₂H₄SC₁₆H₃₃ | |
| " | " | " | " | —COOR₄ | " | |
| " | " | " | " | —CN | —C₃H₆SCH₃ | |
| " | " | " | " | —COOR₄ | " | 135–136 |
| " | " | " | " | —CN | —C₃H₆SC₆H₁₃ | |
| " | " | " | " | —COOR₄ | " | 78–80 |
| " | " | " | " | —CN | —C₃H₆SC₁₂H₂₅ | |
| " | " | " | " | —COOR₄ | " | |
| " | " | " | " | —CN | —C₃H₆SC₁₆H₃₃ | 57–58 |
| " | " | " | " | —COOR₄ | " | |
| " | " | " | " | —CN | —C₄H₈SC₄H₉ | |
| " | " | " | " | —COOR₄ | " | |
| " | " | " | " | —CN | —C₂H₄SC₂H₄SC₂H₅ | |
| " | " | " | " | —COOR₄ | " | |
| " | " | " | " | —CN | —C₄H₈SC₄H₈SC₄H₉ | |
| " | " | " | " | —COOR₄ | " | |
| " | " | " | " | —CN | —C₈H₁₆SC₈H₁₇ | |
| " | " | " | " | —COOR₄ | " | |
| " | " | " | " | —CN | —C₂H₄SC₁₈H₃₇ | |
| " | " | " | " | —COOR₄ | " | |
| " | " | t.butyl | " | —CN | —C₂H₄SC₂H₅ | |
| " | " | " | " | —COOR₄ | " | |
| " | " | " | " | —CN | —C₂H₄SC₃H₇ | |
| " | " | " | " | —COOR₄ | " | |
| " | " | " | " | —CN | —C₂H₄SCH(CH₃)₂ | |
| " | " | " | " | —COOR₄ | " | |
| " | " | " | " | —CN | —C₂H₄SC₄H₉ | |
| " | " | " | " | —COOR₄ | " | |
| " | " | " | " | —CN | —C₂H₄SC₁₈H₃₇ | |
| " | " | " | " | —COOR₄ | " | |
| " | " | " | " | —CN | —C₂H₄SC₆H₁₃ | |
| " | " | " | " | —COOR₄ | " | |
| " | " | " | " | —CN | —C₂H₄SC₈H₁₇ | |
| " | " | " | " | —COOR₄ | " | |
| " | " | " | " | —CN | —C₂H₄SCH₂CH(C₂H₅)—(CH₂)₃CH₃ | |
| " | " | " | " | —COOR₄ | " | |
| " | " | " | " | —CN | —C₂H₄SC₁₂H₂₅ | |
| " | " | " | " | —COOR₄ | " | |
| " | " | " | " | —CN | —C₂H₄SC₁₆H₃₃ | |
| " | " | " | " | —COOR₄ | " | |
| " | " | " | " | —CN | —C₃H₆SC₆H₁₃ | |
| " | " | " | " | —COOR₄ | " | |
| " | " | " | " | —CN | —C₃H₆SC₈H₁₇ | |
| " | " | " | " | —COOR₄ | " | |
| " | " | " | " | —CN | —C₃H₆SC₁₂H₂₅ | |
| " | " | " | " | —COOR₄ | " | |
| " | " | " | " | —CN | —C₃H₆SC₁₆H₃₃ | |
| " | " | " | " | —COOR₄ | " | |
| " | " | " | " | —CN | —C₄H₈SC₄H₉ | |
| " | " | " | " | —COOR₄ | " | |
| " | " | " | " | —CN | —C₂H₄SC₂H₄SC₂H₅ | |
| " | " | " | " | —COOR₄ | " | |
| " | " | " | " | —CN | —C₄H₈SC₄H₈SC₄H₉ | |
| " | " | " | " | —COOR₄ | " | |
| " | " | " | " | —CN | —C₈H₁₆SC₈H₁₇ | |
| " | " | " | " | —COOR₄ | " | |
| " | " | " | " | —CN | —C₂H₄OC₂H₅ | |

TABLE I-continued

| R₁ | R₂ | R₅ | R₆ | R₃ | R₄ | M.P. |
|---|---|---|---|---|---|---|
| " | " | " | " | —COOR₄ | " | |
| " | " | " | " | —CN | —C₂H₄OC₃H₇ | |
| " | " | " | " | —COOR₄ | " | |
| " | " | " | " | —CN | —C₂H₄OCH(CH₃)₂ | |
| " | " | " | " | —COOR₄ | " | |
| " | " | " | " | —CN | —C₂H₄OC₄H₉ | |
| " | " | " | " | —COOR₄ | " | |
| " | " | " | " | —CN | —C₂H₄OC₆H₁₃ | |
| " | " | " | " | —COOR₄ | " | |
| " | " | " | " | —CN | —C₂H₄OC₈H₁₇ | |
| " | " | " | " | —COOR₄ | " | |
| " | " | " | " | —CN | —C₂H₄OCH₂CH(C₂H₅)—(CH₂)₃CH₃ | |
| " | " | " | " | —COOR₄ | " | |
| " | " | " | " | —CN | —C₂H₄OC₁₂H₂₅ | |
| " | " | " | " | —COOR₄ | " | |
| " | " | " | " | —CN | —C₂H₄OC₁₆H₃₃ | |
| " | " | " | " | —COOR₄ | " | |
| " | " | " | " | —CN | —C₂H₄OC₁₈H₃₇ | |
| " | " | " | " | —COOR₄ | " | |
| " | " | " | " | —CN | —C₃H₆OC₃H₇ | |
| " | " | " | " | —COOR₄ | " | |
| " | " | " | " | —CN | —C₃H₆OC₈H₁₇ | |
| " | " | " | " | —COOR₄ | " | |
| " | " | " | " | —CN | —C₃H₆OC₁₂H₂₅ | |
| " | " | " | " | —COOR₄ | " | |
| " | " | " | " | —CN | —C₃H₆OC₁₆H₃₃ | |
| " | " | " | " | —COOR₄ | " | |
| " | " | " | " | —CN | —C₄H₈OC₄H₉ | |
| " | " | " | " | —COOR₄ | " | |
| " | " | " | " | —CN | —C₂H₄OC₂H₄OC₂H₅ | |
| " | " | " | " | —COOR₄ | " | |
| " | " | " | " | —CN | —C₄H₈OC₄H₈OC₄H₉ | |
| " | " | " | " | —COOR₄ | " | |
| " | " | " | " | —CN | —C₈H₁₆OC₈H₁₇ | |
| " | " | " | " | —COOR₄ | " | |
| " | —CH₃ | —CH₃ | —CH₃ | —CN | —C₂H₄OC₂H₅ | |
| " | " | " | " | —COOR₄ | " | |
| " | " | " | " | —CN | —C₂H₄OC₃H₇ | |
| " | " | " | " | —COOR₄ | " | |
| " | " | " | " | —CN | —C₂H₄OCH(CH₃)₂ | |
| " | " | " | " | —COOR₄ | " | |
| " | " | " | " | —CN | —C₂H₄OC₄H₉ | |
| " | " | " | " | —COOR₄ | " | |
| " | " | " | " | —CN | —C₂H₄OC₆H₁₃ | |
| " | " | " | " | —COOR₄ | " | |
| " | " | " | " | —CN | —C₂H₄OC₈H₁₇ | |
| " | " | " | " | —COOR₄ | " | |
| " | " | " | " | —CN | —C₂H₄OCH₂CH(C₂H₅)—(CH₂)₃CH₃ | |
| " | " | " | " | —COOR₄ | " | |
| " | " | " | " | —CN | —C₂H₄OC₁₂H₂₅ | |
| " | " | " | " | —COOR₄ | " | |
| " | " | " | " | —CN | —C₂H₄OC₁₆H₃₃ | |
| " | " | " | " | —COOR₄ | " | |
| " | " | " | " | —CN | —C₂H₄OC₁₈H₃₇ | |
| " | " | " | " | —COOR₄ | " | |
| " | " | " | " | —CN | —C₃H₆OC₃H₇ | |
| " | " | " | " | —COOR₄ | " | |
| " | " | " | " | —CN | —C₃H₆OC₈H₁₇ | |
| " | " | " | " | —COOR₄ | " | |
| " | " | " | " | —CN | —C₃H₆OC₁₂H₂₅ | |
| " | " | " | " | —COOR₄ | " | |
| " | " | " | " | —CN | —C₃H₆OC₁₆H₃₃ | |
| " | " | " | " | —COOR₄ | " | |
| " | " | " | " | —CN | —C₄H₈OC₄H₉ | |
| " | " | " | " | —COOR₄ | " | |
| " | " | " | " | —CN | —C₂H₄OC₂H₄OC₂H₅ | |
| " | " | " | " | —COOR₄ | " | |
| " | " | " | " | —CN | —C₄H₈OC₄H₈OC₄H₉ | |
| " | " | " | " | —COOR₄ | " | |
| " | " | " | " | —CN | —C₈H₁₆OC₈H₁₇ | |
| " | " | " | " | —COOR₄ | " | |
| " | t.butyl | " | t.butyl | —CN | —C₂H₄OC₂H₅ | |
| " | " | " | " | —COOR₄ | " | |
| " | " | " | " | —CN | —C₂H₄OC₃H₇ | |
| " | " | " | " | —COOR₄ | " | |
| " | " | " | " | —CN | —C₂H₄OCH(CH₃)₂ | |
| " | " | " | " | —COOR₄ | " | |
| " | " | " | " | —CN | —C₂H₄OC₄H₉ | |
| " | " | " | " | —COOR₄ | " (17) | 105°C |
| " | " | " | " | —CN | —C₂H₄OC₆H₁₃ | |
| " | " | " | " | —COOR₄ | " | |
| " | " | " | " | —CN | —C₂H₄OC₁₈H₃₇ | |
| " | " | " | " | —COOR₄ | " | |
| " | " | " | " | —CN | —C₂H₄OC₈H₁₇ | |
| " | " | " | " | —COOR₄ | " | |
| " | " | " | " | —CN | —C₂H₄OCH₂CH(C₂H₅)—(CH₂)₃CH₃ | |
| " | " | " | " | —COOR₄ | " | |
| " | " | " | " | —CN | —C₂H₄OC₁₂H₂₅ | |

TABLE I-continued

| R₁ | R₂ | R₅ | R₆ | R₃ | R₄ | M.P. |
|---|---|---|---|---|---|---|
| " | " | " | " | —COOR₄ | " | |
| " | " | " | " | —CN | —C₂H₄OC₁₆H₃₃ | |
| " | " | " | " | —COOR₄ | " | |
| " | " | " | " | —CN | —C₃H₆OC₃H₇ | |
| " | " | " | " | —COOR₄ | " | |
| " | " | " | " | —CN | —C₃H₆OC₈H₁₇ | |
| " | " | " | " | —COOR₄ | " | |
| " | " | " | " | —CN | —C₃H₆OC₁₂H₂₅ | |
| " | " | " | " | —COOR₄ | " | |
| " | " | " | " | —CN | —C₃H₆OC₁₆H₃₃ | |
| " | " | " | " | —COOR₄ | " | |
| " | " | " | " | —CN | —C₄H₈OC₄H₉ | |
| " | " | " | " | —COOR₄ | " | |
| " | " | " | " | —CN | —C₂H₄OC₂H₄OC₂H₅ | |
| " | " | " | " | —COOR₄ | " | |
| " | " | " | " | —CN | —C₄H₈OC₄H₈OC₄H₉ | |
| " | " | " | " | —COOR₄ | " | |
| " | " | " | " | —CN | —C₈H₁₆OC₈H₁₇ | |
| " | " | " | " | —COOR₄ | " | |
| t.butyl | " | t.butyl | " | —CN | —C₂H₄OC₂H₅ | |
| " | " | " | " | —COOR₄ | " (15) | 119–121 |
| " | " | " | " | —CN | —C₂H₄OC₃H₇ | |
| " | " | " | " | —COOR₄ | " | |
| " | " | " | " | —CN | —C₂H₄OCH(CH₃)₂ | |
| " | " | " | " | —COOR₄ | " (16) | 101–103 |
| " | " | " | " | —CN | —C₂H₄OC₄H₉ | |
| " | " | " | " | —COOR₄ | " (18) | 94 |
| " | " | " | " | —CN | —C₂H₄OC₆H₁₃ | |
| " | " | " | " | —COOR₄ | " | |
| " | " | " | " | —CN | —C₂H₄OC₈H₁₇ | |
| " | " | " | " | —COOR₄ | " | |
| " | " | " | " | —CN | —C₂H₄OCH₂CH(C₂H₅)—(CH₂)₃CH₃ | |
| " | " | " | " | —COOR₄ | " | |
| " | " | " | " | —CN | —C₂H₄OC₁₂H₂₅ | |
| " | " | " | " | —COOR₄ | " | |
| " | " | " | " | —CN | —C₂H₄OC₁₈H₃₇ | |
| " | " | " | " | —COOR₄ | " | |
| " | " | " | " | —CN | —C₂H₄OC₁₆H₃₃ | |
| " | " | " | " | —COOR₄ | " | |
| " | " | " | " | —CN | —C₃H₆OC₃H₇ | |
| " | " | " | " | —COOR₄ | " | |
| " | " | " | " | —CN | —C₃H₆OC₈H₁₇ | |
| " | " | " | " | —COOR₄ | " | |
| " | " | " | " | —CN | —C₃H₆OC₁₂H₂₅ | |
| " | " | " | " | —COOR₄ | " | |
| " | " | " | " | —CN | —C₃H₆OC₁₆H₃₃ | |
| " | " | " | " | —COOR₄ | " | |
| " | " | " | " | —CN | —C₄H₈OC₄H₉ | |
| " | " | " | " | —COOR₄ | " | |
| " | " | " | " | —CN | —C₂H₄OC₂H₄OC₂H₅ | |
| " | " | " | " | —COOR₄ | " (19) | 84–86 |
| " | " | " | " | —CN | —C₄H₈OC₄H₈OC₄H₉ | |
| " | " | " | " | —COOR₄ | " | |
| " | " | " | " | —CN | —C₈H₁₆OC₈H₁₇ | |
| " | " | " | " | —COOR₄ | " | |
| " | " | " | " | —H | —CH₃ | |
| —CH₃ | " | " | " | —COOR₄ | —C₁₈H₃₇ (IV) | 87–90 |
| t.butyl | " | " | " | —CN | —CH₂CH=CH₂ | |
| " | " | " | " | —COOR₄ | " | |
| i.propyl | i.propyl | i.propyl | i.propyl | —COOR₄ | —C₂H₄SC₁₂H₂₅ | 72 |
| s.butyl | s.butyl | s.butyl | s.butyl | —COOR₄ | —C₁₈H₃₇ | 50 |
| —CH₃ | t.butyl | i.propyl | i.propyl | —COOR₄ | —C₁₈H₃₇ | 90–93 |

The dialkylbenzyl carboxylic acid esters of the invention are good stabilizers against deterioration by oxygen, light and heat of polymers such as polyolefins, polyamides, shock resistant polystyrene, ABS resins (copolymers of acrylonitrile, butadiene, and styrene), MBS resins (copolymers of methacrylic acid esters, butadiene, and styrene), homopolymers and copolymers of vinyl chloride, and similar resins.

Good stabilizing effects are particularly obtained with compounds of the following formulae

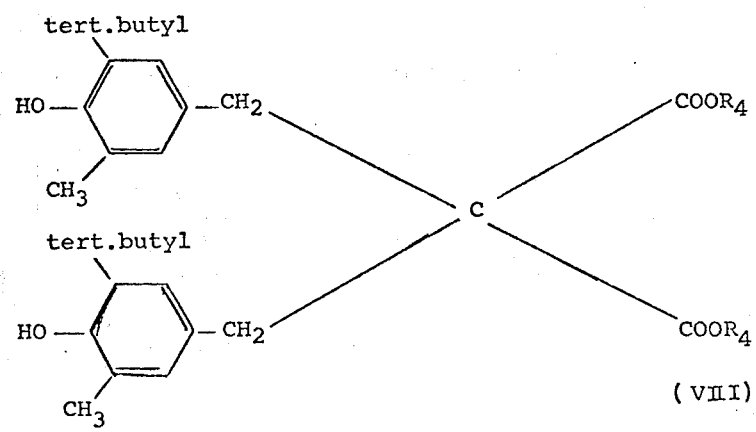

(VII)

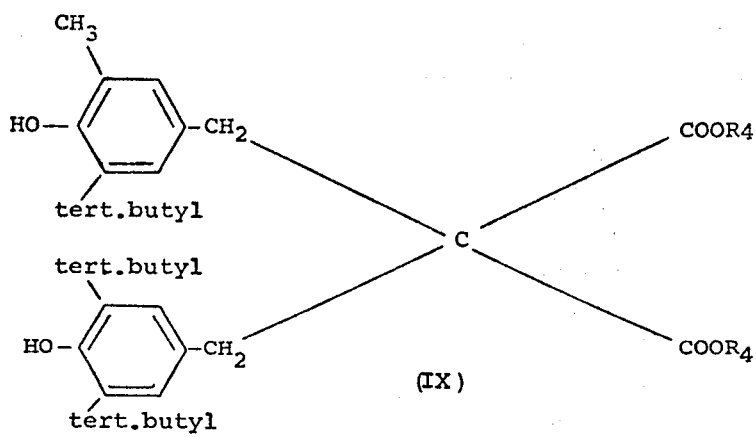

(IX)

and mixtures of these compounds with each other or with sulfur containing stabilizers such as bis esters of thiodipropionic acid. We prefer to use compounds in which the $R_4$ group contains more than 6 carbon atoms and oxygen or sulfur in form of an ether or thioether group. Good stabilizers are also mixtures of said compounds with the compound corresponding to the formula

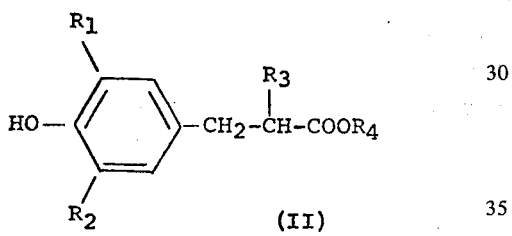

(II)

The novel stabilizers have excellent compatibility with the resins and, due to their low volatility, remain effective even after prolonged thermal exposure of the resin. Generally, they are employed in an amount of 0.01 to 10 percent by weight of the resin. As shown in the examples, they are superior to the esters described e.g. in the German Pat. (DAS) No. 1,201,349 and to the frequently proposed thiobisphenols.

The following examples are given to illustrate the invention but it is to be understood that the resins and stabilizers employed may be substituted by similar compounds and that the scope of the invention is not to be limited to the specific compounds and resins. All parts are by weight, unless indicated otherwise.

EXAMPLE 5

Stabilization of Polypropylene

Four types of unstabilized polypropylene powder, A, B, C, and D were used. For the tests reported in Table II, 100 parts of polypropylene, containing the amounts of stabilizer as indicated, were hot milled at 180°C. for 10 minutes and sheeted off.

The films were piled up and pressed under a pressure of 200 atm. at 210°C.

The obtained plates of 1 mm thickness were cut into 5 strips which were aged in a circulating air oven at 150°C, and the beginning of brittleness was noted.

TABLE II

| Polypropylene | | Stabilizer | Days before begin of oxidative degradation |
|---|---|---|---|
| A | 0.5 | parts 4,4'-thio-bis-(6-tert. butyl-m-cresol) | 11 |
| A | 0.5 | parts β-(3,5-di-tert.butyl-4-hydroxyphenyl)-propionic acid stearyl ester | 46 |
| A | 0.5 | parts Stabilizer I | 75 |
| A | 0.5 | parts Stabilizer V*) | 72 |
| B | 0.3 | parts 4,4-thio-bis-(6-tert. butyl-m-cresol) | 17 |
| B | 0.3 | parts β-(3,5-di-tert.butyl-4-hydroxyphenyl)-propionic acid stearyl ester | 20 |
| B | 0.1 | parts β-(3,5-di-tert.-butyl-4-hydroxyphenyl)-propionic acid stearyl ester + 0.2 parts DLTDP**) | 24 |
| B | 0.3 | parts Stabilizer II | 43 |
| C | 0.3 | parts 4,4-thio-bis-(6-tert. butyl-m-cresol) | 17 |
| C | 0.3 | parts (3-methyl-5-tert.-butyl-4-hydroxy-benzyl)-malonic acid-distearylester | 19 |
| C | 0.3 | parts β-(3,5-di-tert.butyl-4-hydroxy-phenyl)-propionic acid stearylester | 20 |

TABLE II-continued

| Polypropylene | | Stabilizer | Days before begin of oxidative degradation |
|---|---|---|---|
| C | 0.3 parts | Stabilizer I | 19 |
| C | 0.3 parts | Stabilizer 22 | 39 |
| C | 0.3 parts | Stabilizer III | 49 |
| C | 0.3 parts | Stabilizer 24 | 40 |
| D | 0.3 parts | β-(3,5-di-tert.butyl-4-hydroxy-phenyl)-propionic acid stearylester | 74 |
| D | 0.3 parts | Stabilizer 11 | 77 |
| D | 0.3 parts | Stabilizer 12 | 78 |
| D | 0.3 parts | Stabilizer II | 111 |
| D | 0.3 parts | Stabilizer 23 | 111 |

\*\*)dilaurylthiodipropionate
\*)a mixture of 10 parts of Stabilizer I and 90 parts of (4-hydroxy-3-methyl-5-tert.butylbenzyl)-malonic acid distearylester (corresponding to formula II).

Using three different types of unstabilized polypropylene powder, the tests reported in Table III were conducted according to the procedure of Example 5 for Table II except the aging temperature was 140°C.

An unstabilized polypropylene powder was tested using the procedure of Example 5 for Table II, except the plates were subjected to outdoor exposure.

TABLE III

| Polypropylene | | Stabilizer | Days before begin of oxidative degradation |
|---|---|---|---|
| E | | without stabilizer | 1 |
| E | 0.2 parts | 2,6-di-tert.butyl-p-cresol | 1 |
| E | 0.2 parts | Stabilizer 6 | 6 |
| E | 0.2 parts | Stabilizer 7 | 7 |
| F | 0.2 parts | (3-methyl-5-tert.butyl-4-hydroxy-benzyl)-malonic acid-distearyl ester | 32 |
| F | 0.2 parts | Stabilizer 20 | 32 |
| F | 0.2 parts | Stabilizer 21 | 65 |
| F | 0.1 parts | (3-methyl-5-tert.butyl-4-hydroxy-benzyl)-malonic acid-distearylester | 3 |
| F | 0.1 parts | Stabilizer 8 | 6 |
| F | 0.1 parts | Stabilizer 9 | 4 |
| F | 0.1 parts | Stabilizer 10 | 14 |
| F | 0.1 parts | Stabilizer 14 | 9 |
| F | 0.1 parts | Stabilizer 18 | 6 |
| F | 0.1 parts | Stabilizer 20 | 21 |
| F | 0.1 parts | Stabilizer 21 | 13 |
| G | | none | 1 |
| G | 0.1 parts | 2,6-di-tert.butyl-p-cresol | 1 |
| G | 0.1 parts | (3-methyl-5-tert.butyl-4-hydroxy-benzyl)-malonic acid-distearylester | 3 |
| G | 0.1 parts | β-(3,5-di-tert.butyl-4-hydroxy-phenyl)-propionic acid stearylester | 9 |
| G | 0.1 parts | Stabilizer 12 | 9 |
| G | 0.1 parts | Stabilizer 15 | 40 |
| G | 0.1 parts | Stabilizer 16 | 23 |
| G | 0.1 parts | Stabilizer 17 | 44 |
| G | 0.1 parts | Stabilizer 19 | 22 |
| G | 0.1 parts | Stabilizer 21 | 36 |

TABLE IV

| | Stabilizer | Days before beginning of oxidative degradation |
|---|---|---|
| | none | 37 |
| 0.2 parts | (3,5-di-methyl-4-hydroxy-benzyl)-thio-glycolic acid stearylester | 90 |
| 0.2 parts | β-(3,5-di-tert.butyl-4-hydroxy-phenyl)-propionic acid stearylester | 127 |
| 0.2 parts | (3-methyl-5-tert.butyl-4-hydroxy-benzyl)-malonic acid-distearylester | 127 |
| 0.2 parts | Stabilizer 6 | 127 |
| 0.2 parts | Stabilizer 7 | 250 |

EXAMPLE 6

Stabilization of Low Pressure Polyethylene

20 G each of low pressure polyethylene and 20 mg of the stabilizer listed in Table V were processes on a plastograph at 220°C and 30 RPM and the time was noted until the torque dropped, indicating degradation of the polymer.

TABLE V

| Stabilizer | Torque decreased after |
| --- | --- |
| β-(3,5-di-tert.butyl-4-hydroxyphenyl)-propionic acid stearyl ester | 40 ± 2 minutes |
| β-(3,5-di-tert.butyl-4-hydroxyphenyl)-propionic acid stearyl ester + 20 mg DLTDP | 135 + 2 minutes |
| Stabilizer III | 140 + 2 minutes |

The table shows the superiority of the stabilizer of the invention over the known stabilizers of similar type.

100 Parts of low pressure polyethylene, containing 0.02 parts of stabilizer as indicated in Table VI were hot milled at 170° for 10 minutes and sheeted off. The films were piled up and pressed under a pressure of 200 atm. at 180°C.

The plates obtained were of 1mm thickness. These were cut into 5 strips which were aged in a circulating air oven at 130°C, and the beginning of brittleness was noted. The results are reported in Table VI.

TABLE VI

| Stabilizer | became brittle after days |
| --- | --- |
| none | 1 |
| 2,6-di-tert.butyl-p-cresol | 1 |
| (3-methyl-5-tert.butyl-4-hydroxy-benzyl)-malonic acid-distearylester | 2 |
| Stabilizer 13 | 50 |
| Stabilizer 15 | 50 |
| Stabilizer 16 | 59 |
| Stabilizer 17 | 43 |
| Stabilizer 19 | 57 |

EXAMPLE 7

Stabilization of High Pressure Polyethylene

Samples of 100 g of high pressure polyethylene containing the stabilizers reported in Table VII were stored in a drying cabinet at 150°C, and the times to yellow discoloration were determined.

TABLE VII

| | Stabilizer | Hours to beginning of discoloration |
| --- | --- | --- |
| 0.01 parts | 2,6-di-tert.butyl-p-cresol + | 20 |
| 0.01 parts | DLTDP | |
| 0.02 parts | β-(3,5-di-tert.butyl-4-hydroxyphenyl)-propionic acid stearyl ester | 26 |
| 0.02 parts | Stabilizer IV | 28 |
| 0.02 parts | Stabilizer II | 35 |

EXAMPLE 8

Stabilization of Polyamide 100 parts of polyamide containing 1 part of the stabilizers listed in Table VIII were processed on an extruder at 250°C to plates which were divided into 5 strips and subjected to accelerated aging in a drying cabinet at 250°C. The stabilizing effect was determined by the brittleness of the samples.

TABLE VIII

| | Stabilizer | became brittle after days |
| --- | --- | --- |
| 1 part | 4,4'-thio-bis-(6-tert.butyl-m-cresol) | 17 |
| 1 part | β-(3,5-di-tert.butyl-4-hydroxyphenyl) propionic acid stearyl ester | 13 |
| 0.5 parts | copper-II-acetate | |
| 0.5 parts | potassium iodide | 19 |
| 0.5 parts | stabilizer I | |
| 0.5 parts | tris-nonylphenylphosphite | 20 |
| 0.5 parts | stabilizer V | |
| 0.5 parts | tris-nonylphenylphosphite | 22 |

The table shows that the stabilizers of the invention exceed the effectiveness of known antioxidants. An addition of organic phosphite improves further the initial color of the extruded plates.

EXAMPLE 9

Stabilization of an ABS Resin

All the tests hereinafter set forth in Table IX were made with the same ABS polymer which had the approximate composition by weight of 5% acrylonitrile, 15% butadiene, and 80% styrene. Test samples were prepared by hot milling at about 160°C for 10 minutes compositions containing 100 parts of the ABS resin, 1 part of a lubricant (1,2-bis-stearoyl amino ether) and 0.5 parts of the stabilizer. The obtained films were pressed under a pressure of 200 atm. and a temperature of 180°C to plates of 1 mm thickness, which were cut to strips and placed in a drying cabinet at a temperature of 110°C for accelerated aging. The stabilizing efficiency was measured by the change of color and brittleness of the strips. The following results were obtained.

TABLE IX

| Stabilizer | color after 50 days | brittle after days |
|---|---|---|
| 4,4'-thio-bis-(6-tert.butyl-m-cresol) | brown | 40 |
| β-(3,5-di-tert.butyl-4-hydroxy-phenyl-propionic acid stearyl ester | light yellow | 36 |
| Stabilizer II | pale yellow | 43 |

EXAMPLE 10

Stabilization of an MBS Resin

The tests listed in Table X were made with the same MBS polymer which had the approximate composition by weight of 16% methacrylic acid ester, 80% butadiene, and 4% styrene.

Test samples were prepared by hot milling at 170°C for 10 minutes the resin compositions containing the stabilizer and pressing the obtained films in a platen press under a pressure of 200 atm. at a temperature of 190°C to plates of 1 mm thickness which were cut into 5 strips and aged in a drying cabinet at 90°C.

The stabilizing effect was determined by the color changes and brittleness of the strips. The following results were obtained.

TABLE X

| | Stabilizer | Color after 20 days | Brittle after days |
|---|---|---|---|
| 0.5 | parts 4,4'-thio-bis-(6-tert. butyl-m-cresol) | brown | 38 |
| 0.25 0.25 | parts 2,5-di-tert.butyl-p-cresol + parts tris-nonylphenylphosphite | yellow | 57 |
| 0.25 0.25 | parts stabilizer I + parts tris-nonylphenyl-phosphite | light yellow | 65 |
| 0.25 0.25 | parts stabilizer V + parts tris-nonylphenyl-phosphite | light yellow | 62 |

EXAMPLE 11

Stabilization of Impact Resistant Polystyrene

The impact resistant polystyrene was a blend of 88 parts of polystyrene and 12 parts of a butadiene-styrene copolymer which contained as stabilizer 1.2% of tris-nonylphenyl phosphite. 12 g each of said copolymer were plasticized on a laboratory roller mill at 175°C, then 0.15 g of the stabilizer listed in Table XI, and subsequently 88 g of polystyrene were added, and the blends were hot milled at 175°C for 10 minutes and at 180°C and 200 atmospheres pressed to plates which were cut into 5 strips and stored in a drying cabinet at 85°C. The stabilizing effect was determined by the time of beginning brittleness of the samples.

TABLE XI

| STABILIZER | Color after 10 days | Brittle after days |
|---|---|---|
| 4,4'-thio-bis-(6-tert.butyl-m-cresol) | deep yellow | 25 |
| β-(3,5-di-tert.-butyl-4-hydroxy-phenyl)-propionic acid stearyl ester | yellow | 17 |
| Stabilizer II | pale yellow | 25 |

What is claimed is:

1. A compound corresponding to the formula

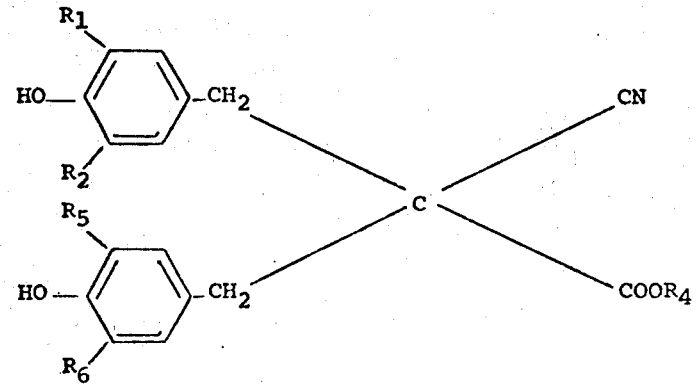

wherein $R_1$, $R_2$, $R_5$ and $R_6$ are alkyl groups having 1 to 6 carbon atoms and $R_4$ is selected from the group consisting of alkyl, straight chain alkenyl, sulfur interrupted alkyl, oxygen interrupted alkyl and aralkyl having up to 20 carbon atoms.

2. A compound of claim 1 wherein $R_4$ is selected from the group consisting of $-C_2H_4SC_2H_5$, $-C_2H_4SC_3H_7$, $-C_2H_4SCH(CH_3)_2$, $-C_2H_4SC_4H_9$, $-C_2H_4SC_6H_{13}$, $-C_2H_4SC_8H_{17}$, $-C_2H_4SCH_2CH(C_2H_5)(CH_2)_3CH_3$, $-C_2H_4SC_{12}H_{25}$, $-C_2H_4SC_{16}H_{33}$, —$C_3H_6SC_3H_7$, —$C_3H_6SC_8H_{17}$, —$C_3H_6SC_{12}H_{25}$, —$C_3H_6SC_{16}H_{33}$, —$C_4H_8SC_4H_9$, —$C_2H_4SC_2H_4SC_2H_5$, —$C_4H_8SC_4H_8SC_4H_9$, —$C_8H_{16}SC_8H_{17}$, and —$C_2H_4SC_{18}H_{37}$.

3. A compound of claim 1 wherein $R_4$ is selected from the group consisting of —$C_2H_4OC_2H_5$, —$C_2H_4OC_3H_7$, —$C_2H_4OCH(CH_3)_2$, —$C_2H_4OC_4H_9$, —$C_2H_4OC_6H_{13}$, —$C_2H_4OC_8H_{17}$, —$C_2H_4OCH_2CH(C_2H_5)(CH_2)_3CH_3$ —$C_2H_4OC_{12}H_{25}$, —$C_2H_4OC_{16}H_{33}$, —$C_3H_6OC_3H_7$, —$C_3H_6OC_8H_{17}$, —$C_3H_6OC_{12}H_{25}$, —$C_3H_6OC_{16}H_{33}$, —$C_4H_8OC_4H_9$, —$C_2H_4OC_2H_4OC_2H_5$, —$C_4H_8OC_4H_8OC_4H_9$, —$C_8H_{16}OC_8H_{17}$ and —$C_2H_4OC_{18}H_{37}$.

4. A compound of claim 1 wherein $R_4$ is selected from the group consisting of —$CH_3$, —$C_2H_5$, —$CH_2(CH_2)_2$, —$C_4H_9$, —$C(CH_3)_3$, —$CH_2CH(CH_3)_2$, —$C_6H_{13}$, —$C_8H_{17}$, —$CH_2CH(C_2H_5)(CH_2)_3CH_3$, —$C_{12}H_{25}$, —$C_{20}H_{41}$, —$C_{16}H_{33}$, 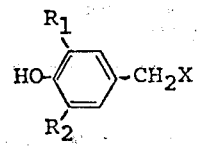

and —$C_{18}H_{37}$.

5. A compound of claim 3 wherein $R_1$, $R_2$, $R_5$ and $R_6$ are tert. butyl.

6. A process of preparing a compound of claim 1 which comprises reacting, in the presence of an alkali metal and an anhydrous inert organic solvent, (a) one mole of

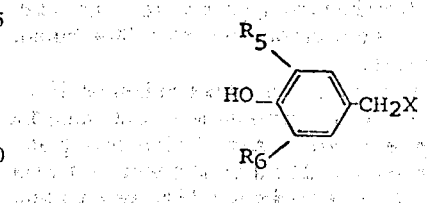

and (b) one mole of with one mole of $NCCH_2COOR_4$ wherein X is halogen.

7. A process according to claim 6 wherein the inert solvent is selected from the groups of aromatic hydrocarbons, aliphatic hydrocarbons and glycol ethers.

* * * * *